United States Patent [19]
Kidd et al.

[11] Patent Number: 5,829,441
[45] Date of Patent: Nov. 3, 1998

[54] CUSTOMIZABLE DENTAL DEVICE FOR SNORING AND SLEEP APNEA TREATMENT

[75] Inventors: Lisa A. Kidd, Leawood, Kans.; Donald M. Lane, Lee's Summit, Mo.

[73] Assignee: Nellcor Puritan Bennett, Pleasanton, Calif.

[21] Appl. No.: 881,292

[22] Filed: Jun. 24, 1997

[51] Int. Cl.⁶ ....................................................... A61F 5/56
[52] U.S. Cl. ........................... 128/848; 128/859; 128/861; 602/902
[58] Field of Search ..................... 128/846, 848, 128/859–862; 602/902

[56] References Cited

U.S. PATENT DOCUMENTS

| | | | |
|---|---|---|---|
| Re. 33,442 | 11/1990 | George | 128/860 |
| 746,869 | 12/1903 | Moulton . | |
| 1,076,534 | 10/1913 | Wallen . | |
| 1,146,264 | 7/1915 | Kelly . | |
| 1,649,664 | 11/1927 | Carter . | |
| 1,674,336 | 6/1928 | King . | |
| 2,171,695 | 9/1939 | Harper | 32/19 |
| 2,424,533 | 7/1947 | Faires . | |
| 2,521,039 | 9/1950 | Carpenter | 128/136 |
| 2,531,222 | 11/1950 | Kesling | 32/14 |
| 2,590,118 | 3/1952 | Oddo, Jr. | 128/136 |
| 2,833,278 | 5/1958 | Ross | 128/136 |
| 2,882,893 | 4/1959 | Godfroy | 128/136 |
| 3,124,129 | 3/1964 | Grossberg | 128/136 |
| 3,321,832 | 5/1967 | Weisberg | 32/32 |
| 3,434,470 | 3/1969 | Strickland | 128/136 |
| 3,457,916 | 7/1969 | Wolicki | 128/136 |
| 3,513,838 | 5/1970 | Foderick et al. | 128/136 |
| 3,864,832 | 2/1975 | Carlson | 128/136 |
| 3,871,370 | 3/1975 | McDonald | 128/136 |
| 4,016,650 | 4/1977 | Leusner et al. | 32/17 |
| 4,026,024 | 5/1977 | Tradowsky | 32/19 |
| 4,114,614 | 9/1978 | Kesling | 128/136 |
| 4,182,312 | 1/1980 | Mushabac | 433/68 |
| 4,227,877 | 10/1980 | Tureaud et al. | 433/41 |
| 4,304,227 | 12/1981 | Samelson | 128/136 |
| 4,376,628 | 3/1983 | Aardse | 433/42 |
| 4,439,147 | 3/1984 | Magill et al. | 433/3 |

(List continued on next page.)

FOREIGN PATENT DOCUMENTS

| | | |
|---|---|---|
| 359135 | 3/1990 | European Pat. Off. . |
| 2320501 | 11/1974 | Germany . |
| 3707952 | 9/1988 | Germany . |
| 1569129 | 6/1980 | United Kingdom . |

OTHER PUBLICATIONS

Mayo Clinic Health Letter; vol. 13, No. 7, Jul. 1996.
Farrar et al.; A Clinical Outline of Termporomandibular Joint Diagnosis and Treatment; *Normandie Study Group for TMJ Dysfunction*, 7th Ed. Normandie Publications (1983).
Brochure of Professional Positioners covering orthodontic appliances (1984).

*Primary Examiner*—Michael A. Brown
*Attorney, Agent, or Firm*—Hovey, Williams, Timmons & Collins

[57] ABSTRACT

A mandible extension dental device (10) is provided which includes adjustable upper and lower arch trays (12, 14) and coupling means (16) designed to pull the lower jaw of a user forwardly during sleep, so as to minimize snoring and mild apnea conditions. Each of the arch trays (12, 14) includes a substantially rigid synthetic body (18, 38) equipped with a pair of generally L-shaped, continuous adjustment slots (32, 34 and 46, 48). Thermoplastic molding material (36, 60) within each tray (12, 14) permits custom fitting of the trays (12, 14) to the upper and lower arches of a patient. During such fitting, the tray bodies (18, 38) are adjusted as necessary owing to the provision of the slots (32, 34 and 46, 48) to accommodate the arch configurations of the patient. Once the material (36, 60) hardens, the patient-specific arch configurations are permanently retained. The device (10) can be rapidly fitted in the field without the need for the services of a dentist. The coupling means (16) can be infinitely adjusted while the device (10) is in the patient's mouth, to insure the most comfortable fit consistent with lower jaw extension.

22 Claims, 3 Drawing Sheets

U.S. PATENT DOCUMENTS

| | | | |
|---|---|---|---|
| 4,495,945 | 1/1985 | Liegner | 128/136 |
| 4,505,672 | 3/1985 | Kurz | 433/6 |
| 4,553,549 | 11/1985 | Pope et al. | 128/421 |
| 4,568,280 | 2/1986 | Ahlin | 433/6 |
| 4,569,342 | 2/1986 | von Nostitz | 128/136 |
| 4,593,686 | 6/1986 | Lloyd et al. | 128/136 |
| 4,602,905 | 7/1986 | O'Keefe, III | 433/41 |
| 4,639,220 | 1/1987 | Nara et al. | 433/69 |
| 4,655,213 | 4/1987 | Rapoport et al. | 128/205.25 |
| 4,715,368 | 12/1987 | George | 128/136 |
| 4,773,853 | 9/1988 | Kussick | 433/6 |
| 4,799,500 | 1/1989 | Newbury | 128/859 |
| 4,862,903 | 9/1989 | Campbell | 128/861 |
| 4,901,737 | 2/1990 | Toone | 128/848 |
| 4,919,128 | 4/1990 | Kopala et al. | 128/207.18 |
| 4,932,867 | 6/1990 | Uemo | 433/69 |
| 4,955,393 | 9/1990 | Adell | 128/859 |
| 5,003,994 | 4/1991 | Cook | 128/848 |
| 5,018,533 | 5/1991 | Hawkins | 128/848 |
| 5,028,232 | 7/1991 | Snow | 433/24 |
| 5,042,506 | 8/1991 | Liberati | 128/848 |
| 5,056,534 | 10/1991 | Wright | 128/848 |
| 5,078,600 | 1/1992 | Austin | 433/73 |
| 5,092,346 | 3/1992 | Hays et al. | 128/848 |
| 5,103,838 | 4/1992 | Yousif | 128/859 |
| 5,117,816 | 6/1992 | Shapiro et al. | 128/200.24 |
| 5,183,057 | 2/1993 | Syrop et al. | 128/845 |
| 5,188,529 | 2/1993 | Liith | 433/68 |
| 5,267,862 | 12/1993 | Parker | 433/215 |
| 5,277,202 | 1/1994 | Hays | 128/848 |
| 5,313,960 | 5/1994 | Tomasi | 128/848 |
| 5,365,945 | 11/1994 | Halstrom | 128/848 |
| 5,427,117 | 6/1995 | Thornton | 128/848 |
| 5,499,633 | 3/1996 | Fenton | 128/848 |
| 5,537,994 | 7/1996 | Thornton | 128/204.18 |
| 5,566,683 | 10/1996 | Thornton | 128/848 |
| 5,570,704 | 11/1996 | Buzzard | 128/848 |

CUSTOMIZABLE DENTAL DEVICE FOR SNORING AND SLEEP APNEA TREATMENT

BACKGROUND OF THE INVENTION

1. Field of the Invention

The present invention is broadly concerned with an improved dental device used in the treatment of snoring conditions and mild sleep apnea. More particularly, the invention pertains to such a dental device which provides upper and lower arch trays respectively fitted to a user's upper and lower teeth, with a selectively adjustable coupling means for extension of the user's jaw; the arch trays of the invention are advantageously formed with adjustment slots therein permitting alteration of the arch dimensions and configurations thereof during normal molding of the trays about the user's teeth, thereby permitting use of the trays with patients having varying arch dimensions. In addition, the dental device of the invention is provided with a compact adjustment mechanism which can be easily adjusted while the device is worn by the patient, so as to permit the most precise and comfortable setting.

2. Description of the Prior Art

Many individuals experience difficulty in sleeping because of breathing problems. These difficulties include excessive snoring and the potentially much more serious problem of sleep apnea. Serious sleep apnea disorders are often treated by the application of constant positive pressure (CPAP) air delivered to the patient through a face or nose mask. However, less severe forms of sleep apnea or snoring conditions can be successfully treated by dental devices effective for forward extension of the mandible of the patient during sleep. This serves to maintain the patient's airway fully open by preventing the soft tissue of the throat and tongue from collapsing into the airway, to thus ameliorate the patient's breathing problems.

U.S. Pat. Nos. 5,566,683, 5,427,117 and 5,537,994 describe dental devices designed for mandible extension. The devices illustrated in these patents are generally designed for custom fitting by a dentist in order to achieve the best possible fit and adjustment. Normally, the dentist is required to take a dental impression which is a time-consuming and costly process. Also, the fitting dentist or dental laboratory would stock a series of arch trays having varying arch dimensions and configurations, in the hope that almost all individuals can be properly fitted. However, the necessity for purchasing and stocking multiple tray styles and the professional fitting of these devices necessarily increases the treatment cost to the user.

It is also important that mandible extension dental devices be as small as possible so as to not retard flow of air through the patient's airway or to extend into the normal tongue space of the patient. This in turn means that the arch trays and adjustment mechanism provided with such dental devices must be as compact as possible. Moreover, manipulation of the adjustment mechanism should be relatively easy and possible while the device is being worn by the patient. As can be appreciated, if the device can only be adjusted outside of the patient's mouth, precise adjustment can be difficult or impossible to achieve.

There is accordingly a need in the art for an improved mandible extension dental device which can be fitted by a technician or even the user so as to avoid the necessity of custom fitting by a dentist, and which avoids the problems associated with multiple arch tray sizes and difficult, out-of-mouth adjustments.

SUMMARY OF THE INVENTION

The present invention overcomes the problems outlined above and provides a dental device including upper and lower, generally U-shaped arch trays equipped with selectively operable coupling means for mandible extension in use. Preferably, each of the upper and lower arch trays includes deformable (usually thermoplastic) material therein moldable about at least some of a user's upper and lower teeth respectively, with subsequent setting and hardening of the molded material. In addition, each of the arch trays is provided with one or more elongated adjustment slots therein which allows selective flexure and alteration of the arch configurations of the trays during the initial molding and fitting thereof to the patient, with the trays retaining their altered arch configurations after setting and hardening of the molded material. In this fashion, universal upper and lower arch trays can be provided which can comfortably fitted to a variety of patients having different arch dimensions.

In particularly preferred forms, each of the upper and lower trays is in the form of a generally U-shaped tray body formed of synthetic resin material and having a supply of thermoplastic molding material (e.g., a mixture of ethylene-vinyl acetate copolymer and polycaprolactone) therein; these trays are further equipped with a pair of spaced, generally L-shaped adjustment slots each having a width of from about 0.03–0.10 inches. In use, the trays are first heated and applied to the upper and lower teeth of the patient. During this operation, synthetic resin molding material is flowable and workable, and is molded about the patient's teeth. At the same time, the respective trays can be adjusted to conform to the particular arch configurations of the patient, owing to the provision of the adjustment slots therein. However, upon cooling of the molded material and resetting thereof as a hardened mass, the adjustment of the trays is likewise set and permanently maintained.

The dental device of the invention is equipped with an improved adjustment structure for selective extension of a user's lower jaw. Such adjustment structure comprises an elongated guide secured to the lower surface of the upper tray and a shiftable element slidably supported on the guide and including a depending coupler. The guide and element cooperatively present a dovetail joint therebetween. An elongated thrust screw is operatively coupled with the slidable element for selective fore and aft adjustment of the latter upon rotation of the thrust screw. The lower tray of the device is equipped with means for interfitting with the depending coupler. In preferred forms, the lower tray has a small web adjacent the upper surface thereof for this purpose.

DETAILED DESCRIPTION OF THE PREFERRED EMBODIMENT

Figure 1:
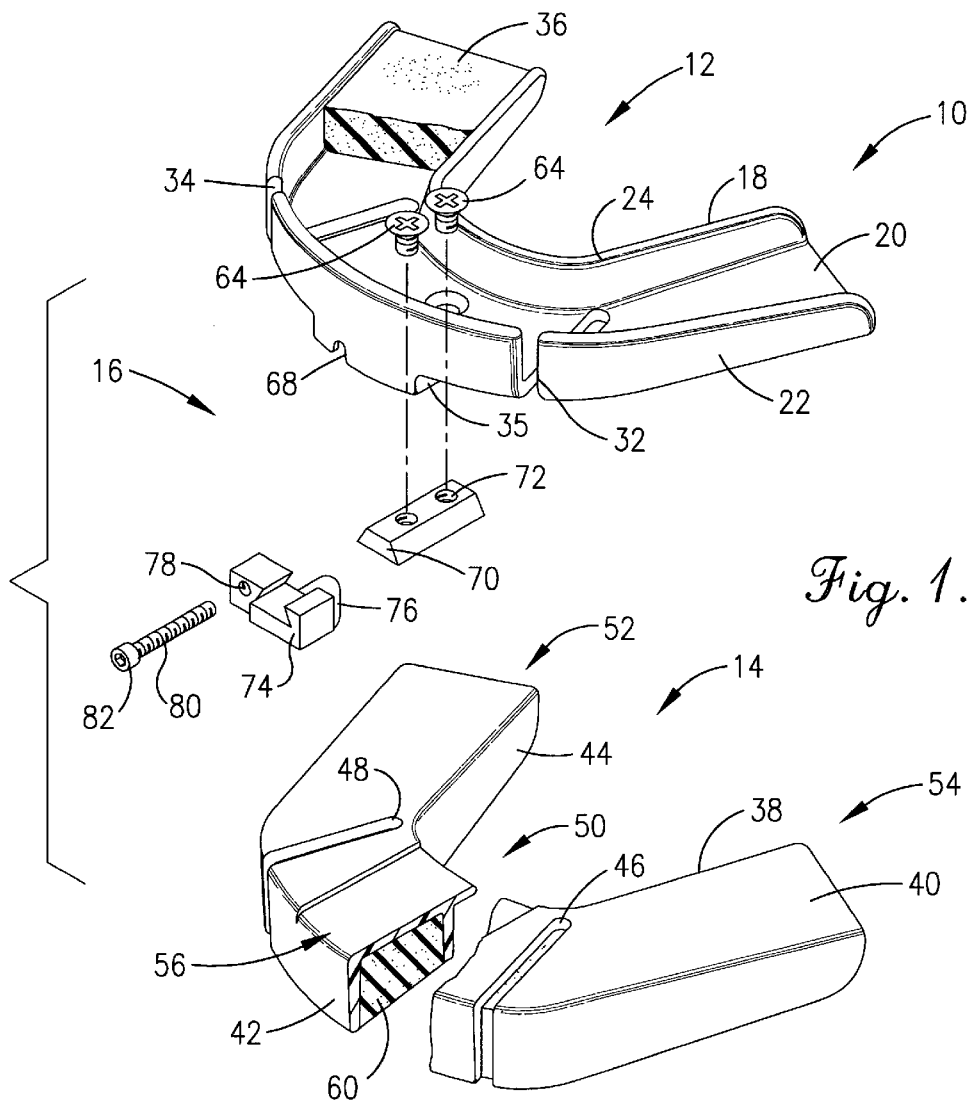
FIG. 1 is a fragmentary exploded view of the preferred dental device of the invention.
Figure 2:
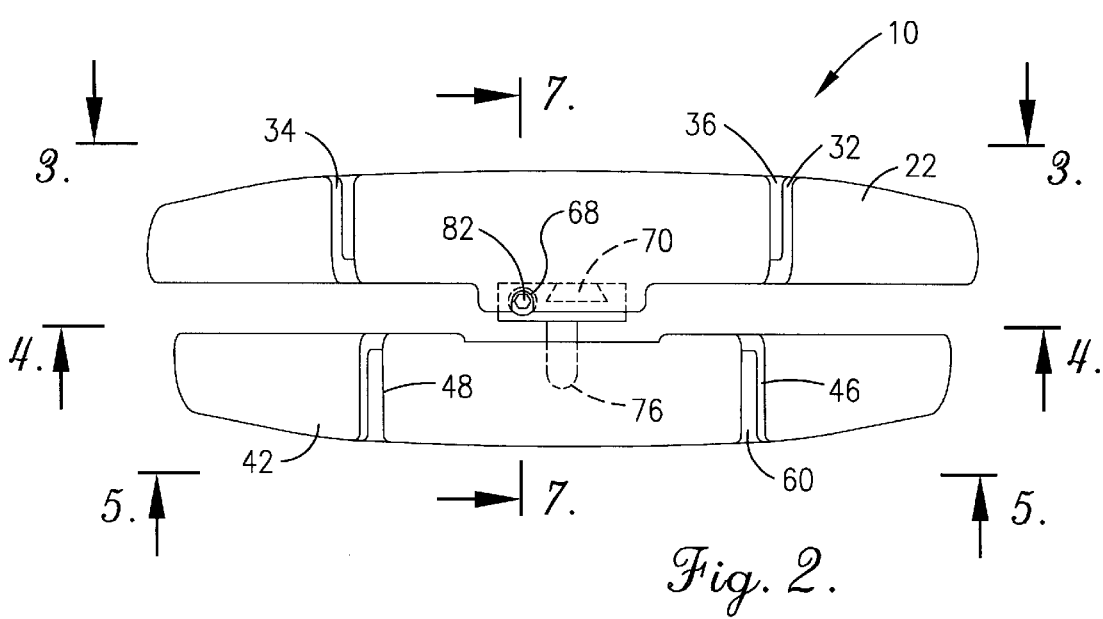
FIG. 2 is a front elevational view of the dental device, showing the upper and lower trays thereof coupled together.

Turning now to the drawings, and particularly FIGS. 1–2, a dental device 10 is illustrated. Broadly, the device 10 includes an upper arch tray 12, lower arch tray 14, and coupling assembly 16 designed for interconnecting the upper and lower arch trays 12, 14 in a patient's mouth.

Figure 3:
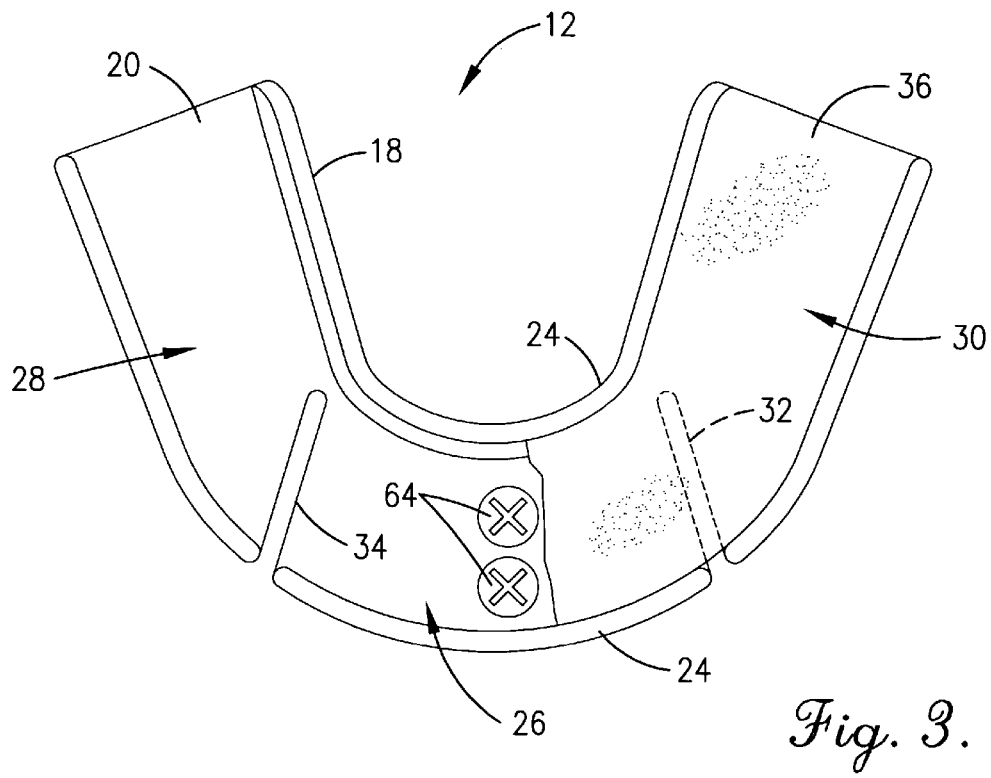
FIG. 3 is a top view of the preferred upper arch tray of the invention taken along line 3—3 of FIG. 2, with a portion of the molding material therein removed to reveal the structure of the tray.
Figure 4:
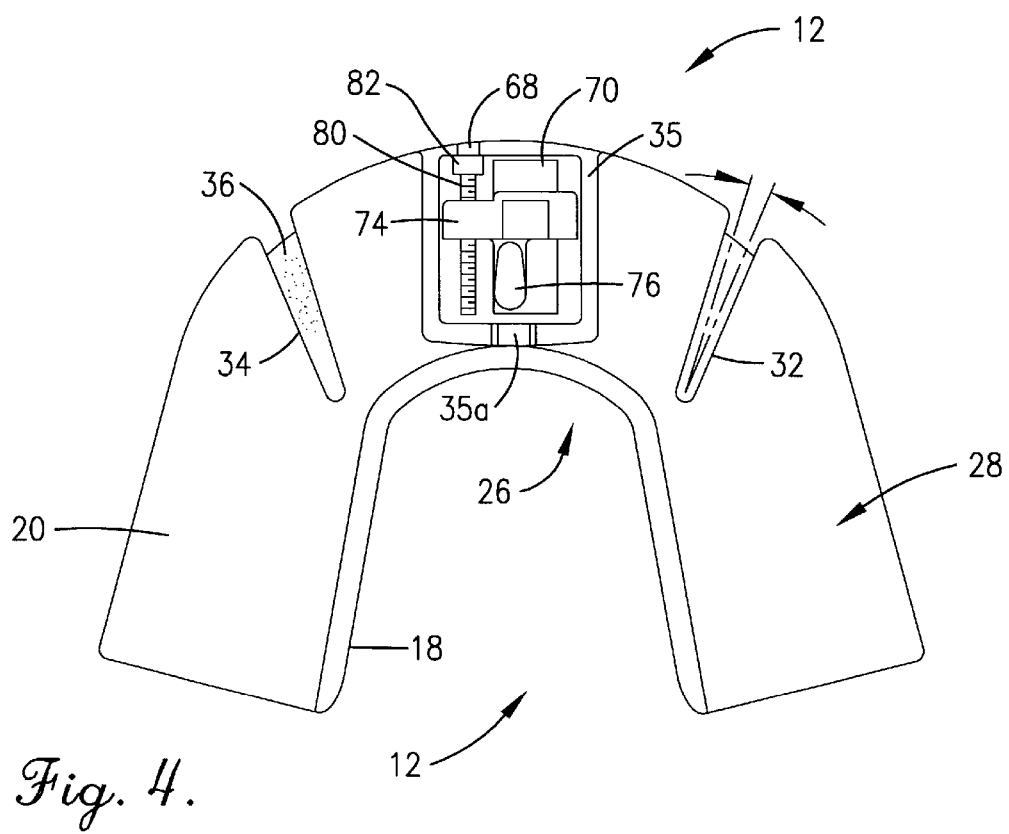
FIG. 4 is a bottom view of the preferred upper arch tray of the invention taken along line 4—4 of FIG. 2 and illustrating the preferred adjustment mechanism.

In more detail, the upper arch tray 12 is in the form of a generally U-shaped in plan synthetic resin body 18 presenting a substantially flat base panel 20 as well as upstanding, opposed, front and rear sidewall segments 22, 24. The body 18 is advantageously formed from polycarbonate material, e.g., Lexan HP polycarbonate resin. As best seen in FIG. 3, the body 18 presents a central, generally arcuate bight 26 with a substantially straight leg member 28, 30 extending from the bight ends; it will be observed that the leg members 28, 30 diverge from each other (see FIGS. 3–4). The body 18 is also equipped with a pair of generally L-shaped, continuous adjustment slots 32, 34 which are located proximal to the ends of the bight 26. Each slot 32, 34 extends from the top of front sidewall segment 22 downwardly through the full height thereof and then extends laterally for a substantial portion of the width of base panel 20. Each slot 32, 34 has a width of about 0.03–0.1 inches, most preferably about 0.07 inches. As best seen in FIG. 4, the lower surface of base panel 20 is provided with an integral, forwardly open, depending U-shaped flange 35 having a central recess 35a. The importance of this feature will be explained hereafter.

The open top, generally U-shaped tray region defined by arch tray 12 is filled with a deformable thermoplastic molding material 36. This material can be selected from a number of possible candidates, but preferably the material is thermoplastic under moderate heating for molding about a patient's teeth, but which will reset to a hardened mass after cooling. The most preferred molding material 36 is made up of equal weight proportions of ethylene-vinyl acetate (EVA) copolymer and polycaprolactone. The preferred EVA material is DuPont Elvax 150, whereas the polycaprolactone is preferably Union Carbide Tone Polymer P767.

Figure 5:
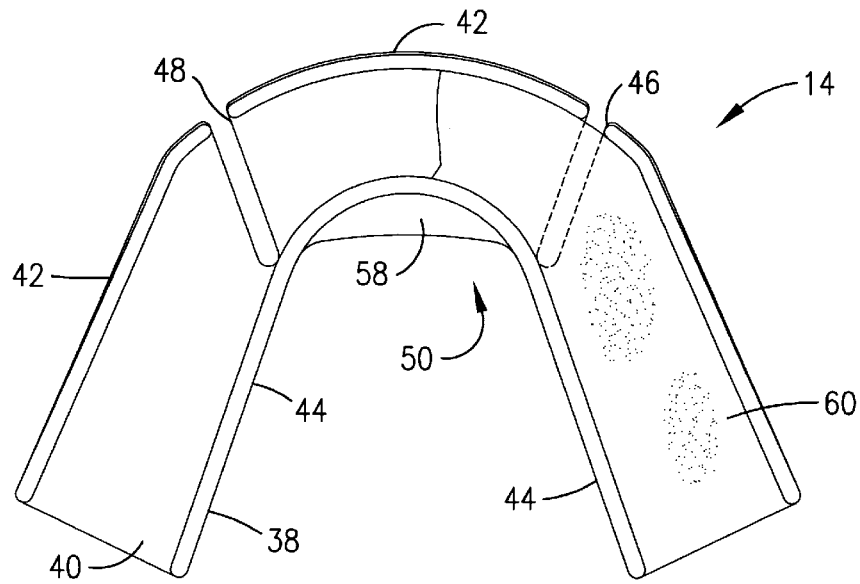
FIG. 5 is a bottom view of the preferred lower arch tray of the invention taken along line 5—5 of FIG. 2, with a portion of molding material therein removed.
Figure 7:
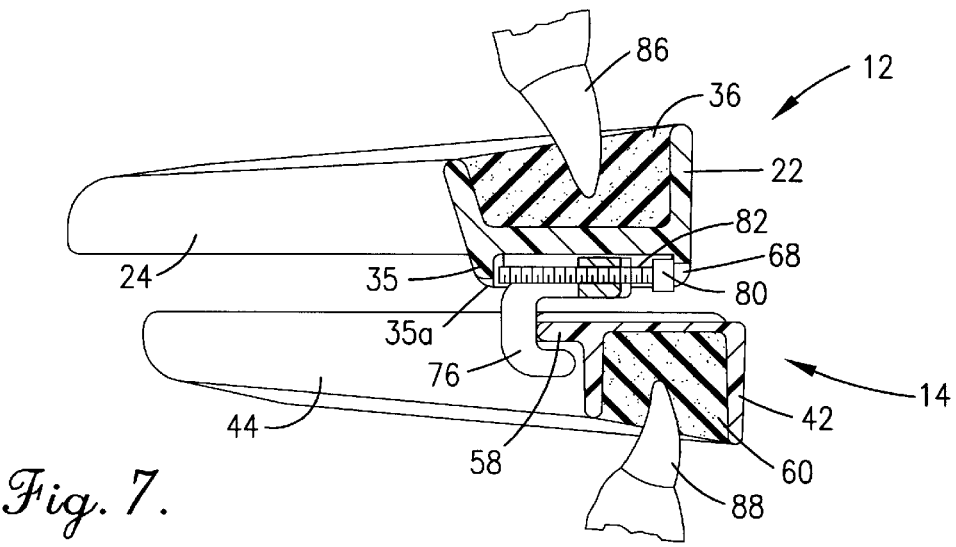
FIG. 7 is a vertical sectional view taken along line 7—7 of FIG. 2 and illustrating the device of the invention installed on a patient's upper and lower teeth and depicting the interfitting of the upper and lower arch trays and consequent mandible extension of the patient.

The lower arch tray 14 is in many respects similar to tray 12 and likewise is in the form of a polycarbonate body 38 having a base panel 40 and upstanding, opposed front and rear sidewall segments 42, 44. The body 38 also has a pair of spaced apart, generally L-shaped adjustment slots 46, 48 extending from the bottom margin of the sidewall 42 throughout the full height thereof, and then rearwardly for substantially the full width of the base panel 40; the slots 46, 48 are moreover located proximal to the ends of the central bight 50 of the body 38 adjacent the diverging leg members 52, 54 thereof. As best seen in FIG. 1, the upper surface of base panel 40 presents a relieved region 56 extending the full width of the base panel. This region 56 generally corresponds with, though is somewhat wider than, the flange 35 of upper arch tray 12. A small, rearwardly extending web 58 is provided within the bight 50 of the body 38 as best seen in FIGS. 5 and 7. The lower arch tray 14 is also filled with deformable molding material 60 identical with the material 36 described previously.

The coupling assembly 16 includes an elongated dovetail guide 70 which is also secured within the U-shaped flange recess by means of the screws 64, the latter extending through panel 20 and into tapped bores 72 provided in the guide. A complemental dovetail shiftable element 74 is mounted on the guide 70 for fore and aft movement thereof. The element 74 carries a depending hook 76 and is also provided with a threaded opening 78. A thrust screw 80 is situated within opening 78 and has an Allen-type head 82. As best seen in FIG. 2, the head 82 is located in the region of a formed recess 68 so as to allow access to the head 82.

Figure 6:
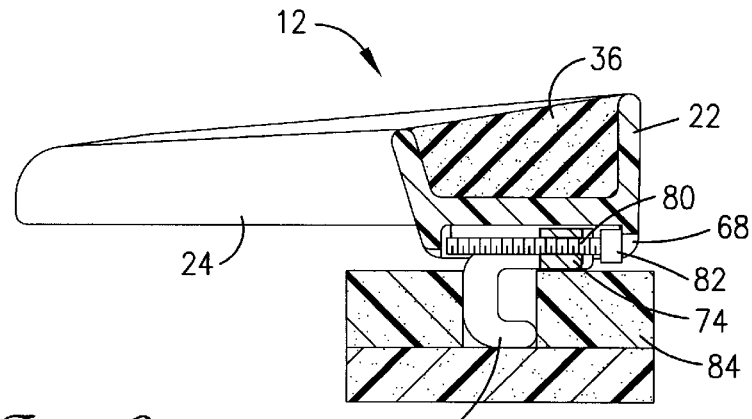
FIG. 6 is a vertical sectional view of the preferred upper arch tray, illustrating an initial step in fitting thereof with the use of a removable protective pad disposed over the depending hook coupler thereof.

In the use of device 10, a temporary disposable foam pad 84 (FIG. 6) is placed over the hook 76. For this purpose, the pad 84 is provided with adhesive for temporarily holding the pad in place. Next, the arch tray 12 is placed in warm water (165°–185° F.) to soften the molding material 36. When this becomes completely translucent, the tray is removed from the water and excess water is shaken off. The arch tray 12 is then placed in the mouth of the patient with the front teeth 86 as far forward as possible. Normally, the arch tray 12 is first firmly placed over the back teeth and then over the front teeth. The arch tray 12 is then removed by gripping the polycarbonate body 18 while avoiding touching the material 36. Any material 36 that has extended over the edges of the body 18 is then removed by scissors, with the exception of any material which extends out of the back of the tray around the last molars. The arch tray is then placed back in the water bath to soften the material again and the latter is then smoothed by finger pressure. The tray is then placed back in the mouth of the patient and pressed (especially in the back) with even pressure, avoiding any "rocking" of the arch tray. The arch tray is then removed from the mouth and excess material 36 is trimmed. At this point, the arch tray 12 is then placed back in the mouth of the patent and allowed to set for a few minutes. Finally, the arch tray 12 is removed from the mouth of the patient and allowed to cool for a few minutes in an ice bath. The above procedure is repeated with the lower arch tray 14 to mold latter relative to the patient's lower teeth 88, with the exception that no temporary foam pad is required.

During the molding operations with the arch trays 12, 14, the arch configurations of the bodies 18 and 38 are altered to properly fit the patient. In this regard, during the time when the molding material 36, 60 is soft, the bodies 18, 38 can be readily flexed at the joints defined by the slots 32, 34 and 46, 48; such flexure is illustrated by the arrow lines adjacent slot 32 in FIG. 4. The width of these adjustment slots accommodates this change in configuration, which is sufficient to fit essentially all patients. Once the arch trays 12, 14 have been fitted and the molding material therein cooled and set, the bodies 18, 38 permanently retain their patient-specific configurations.

The patient is next instructed to relax his jaw in a comfortable breathing position with lips together, so that the teeth are slightly separated; the lower jaw should be slightly forward relative to its position when the jaw is clenched. The arch trays 12, 14 are then inserted into the patient's mouth (pad 84 is removed for this purpose) and the patient is instructed to return his jaw to the relaxed condition. The hook 76 is then adjusted to hold the patient's jaw in this position, i.e., the hook is positioned to engage web 58 as best seen in FIG. 7. As can be appreciated, an infinite adjustment can be readily effected while the device 10 is in the patient's mouth by use of an appropriate Allen tool to rotate the screw 80 to either move the hook forwardly or rearwardly as required. During further use of the device 10, the patient may incrementally adjust the hook 76 forwardly until the sleep disturbing condition is relieved. Once the snoring or mild apnea symptoms are ameliorated, no further adjustment of the device 10 is required.

I claim:

1. An arch tray comprising:

a generally U-shaped body presenting a base panel and a pair of spaced, opposed, marginal sidewall segments each having a respective outer margin spaced from said base panel, said base panel and sidewall segments cooperatively defining a tray region;

a thermoplastic molding material within said tray region, said molding material being substantially rigid at room temperature but, upon heating thereof, becoming sufficiently soft and workable to allow molding of the material around a user's teeth with resetting and hardening of the molded material after cooling thereof, said body presenting an elongated adjustment slot therein oriented for permitting selective alteration of the arch configuration of said body when said molding material is heated, and subsequent setting of the body at an altered arch configuration upon said hardening of the molding material in order to allow use thereof with a variety of users having different arch dimensions, at least a portion of said slot being located in one of said sidewall segments.

2. The arch tray of claim 1, said adjustment slot being substantially L-shaped in configuration.

3. The arch tray of claim 1, including a pair of said adjustment slots.

4. The arch tray of claim 1, said body presenting an arcuate central bight having a pair of spaced, opposed ends and a leg member extending from each opposed end of said bight, said leg members diverging from each other, there being a pair of adjustment slots respectively located proximal to said bight ends.

5. The arch tray of claim 4, said adjustment slots each being generally L-shaped in configuration and extending from an outer margin of one of said sidewall segments through the entirety of the one sidewall segment and through a substantial portion of said base panel.

6. The arch tray of claim 5, each of said slots having a width of from about 0.03–0.10 inches.

7. The arch tray of claim 1, said synthetic resin material comprising a mixture of ethylene-vinyl acetate copolymer and polycaprolactone.

8. A dental device comprising:

an upper arch tray including a generally U-shaped first tray body having a first thickness and a deformable material therein moldable about at least some of a user's upper teeth, with subsequent setting and hardening of the molded material;

a lower arch tray including a generally U-shaped second tray body having a second thickness and a deformable material therein moldable about at least some of a user's lower teeth, with subsequent setting and hardening of the molded material; and means for selectively coupling said upper and lower arch trays when the latter are installed on the user's upper and lower teeth respectively, said coupling means including adjustment structure for selective extension of the user's lower jaw, said first and second tray bodies each presenting an elongated adjustment slot therein oriented for permitting selective alteration of the arch configuration of the first and second bodies when said molding material therein is molded about a user's upper and lower teeth, with said bodies retaining said altered arch configuration after said setting and hardening of said molding material, in order to allow use thereof with a variety of users having different arch dimensions, the adjustment slot of each of said first and second tray bodies extending through said first and second thicknesses respectively to form through openings.

9. The dental device of claim 8, each of said adjustment slots being substantially L-shaped in configuration.

10. The dental device of claim 8, each of said first and second bodies including a pair of said adjustment slots.

11. The dental device of claim 8, each of said first and second bodies presenting an arcuate central bight having a pair of spaced, opposed ends and a leg member extending from each opposed end of said bight, said leg members diverging from each other, there being a pair of adjustment slots respectively located proximal to said bight ends.

12. The dental device of claim 8, said adjustment slots each being generally L-shaped in configuration and extending from an outer margin of one of said sidewall segments through the entirety of the one sidewall segment and through a substantial portion of said base panel.

13. The dental device of claim 12, each of said slots having a width of from about 0.03–0.10 inches.

14. The dental device of claim 8, said synthetic resin material comprising a mixture of ethylene-vinyl acetate copolymer and polycaprolactone.

15. A dental device comprising:

an upper arch tray fitting at least some of a user's upper teeth and presenting a lower surface;

a lower arch tray fitting at least some of a user's lower teeth and presenting an upper surface; and means for selectively coupling said upper and lower arch trays when the latter are installed on the user's upper and lower teeth respectively, said coupling means including adjustment structure for selective extension of the user's lower jaw and comprising elongated guide operatively secured to said lower surface of said upper tray;

a shiftable element slidably supported on said guide and including a depending coupler, said guide and element cooperatively presenting a dovetail joint therebetween;

an elongated thrust screw operatively coupled with said slidable element for selective fore and aft adjustment of said element upon rotation of the thrust screw; and means carried by said lower tray for interfitting with said coupler.

16. A dental device comprising:

an upper arch tray including thermoplastic molding material adapted for molding about at least some of a user's upper teeth, with subsequent setting and hardening of the molded material;

a lower arch tray including thermoplastic molding material adapted for molding about at least some of a user's lower teeth, with subsequent setting and hardening of the molded material; and means for selectively coupling said upper and lower arch trays when the latter are installed on the user's upper and lower teeth respectively, said coupling means including adjustment structure for selective extension of the user's lower jaw, said upper and lower trays each presenting an elongated adjustment slot therein which extends through the entire thickness of the respective tray to define a through opening, each adjustment slot oriented for permitting selective alteration of the arch configuration of the upper and lower arch trays when said molding material of the upper and lower arch trays is molded about said upper and lower teeth respectively, with setting of the upper and lower arch trays at respectively altered arch configurations upon setting and hardening of the molded material therein, in order to allow use of the upper and lower arch trays with a variety of users having different arch dimensions.

17. An arch tray comprising:

a generally U-shaped body presenting a base panel and a pair of spaced, opposed, marginal sidewall segments each having a respective outer margin spaced from said base panel, said base panel and sidewall segments cooperatively defining a tray region; and a thermoplastic molding material within said tray region, said molding material being substantially rigid at room temperature but, upon heating thereof, becoming sufficiently soft and workable to allow molding of the material around a user's teeth with resetting and hardening of the molded material after cooling thereof, said body presenting an elongated adjustment slot of substantially L-shaped configuration therein oriented for permitting selective alteration of the arch configuration of said body when said molding material is heated, and subsequent setting of the body at an altered arch configuration upon said hardening of the molding material in order to allow use thereof with a variety of users having different arch dimensions.

18. An arch tray comprising:

a generally U-shaped body presenting a base panel and a pair of spaced, opposed, marginal sidewall segments each having a respective outer margin spaced from said base panel, said base panel and sidewall segments cooperatively defining a tray region, said body further presenting an arcuate central bight, having a pair of spaced, opposed ends and a leg member extending from each opposed end of said bight, said leg members diverging from each other; and a thermoplastic molding material within said tray region, said molding material being substantially rigid at room temperature but, upon heating thereof, becoming sufficiently soft and workable to allow molding of the material around a user's teeth with resetting and hardening of the molded material after cooling thereof, said body presenting a pair of elongated adjustment slots therein respectively located proximal to said bight ends and oriented for permitting selective alteration of the arch configuration of said body when said molding material is heated, and subsequent setting of the body at an altered arch configuration upon said hardening of the molding material in order to allow use thereof with a variety of users having different arch dimensions.

19. An arch tray comprising:

a generally U-shaped body presenting a base panel and a pair of spaced, opposed, marginal sidewall segments each having a respective outer margin spaced from said base panel, said base panel and sidewall segments cooperatively defining a tray region; and a thermoplastic molding material within said tray region, said molding material being substantially rigid at room temperature but, upon heating thereof, becoming sufficiently soft and workable to allow molding of the material around a user's teeth with resetting and hardening of the molded material after cooling thereof, said body presenting an elongated adjustment slot therein oriented for permitting selective alteration of the arch configuration of said body when said molding material is heated, and subsequent setting of the body at an altered arch configuration upon said hardening of the molding material in order to allow use thereof with a variety of users having different arch dimensions, said adjustment slot being generally L-shaped in configuration and extending from an outer margin of one of said sidewall segments through the entirety of the one sidewall segment and through a substantial portion of said base panel.

20. A dental device comprising:

an upper arch tray including a generally U-shaped first tray body having a deformable material therein moldable about at least some of a user's upper teeth, with subsequent setting and hardening of the molded material;

a lower arch tray including a generally U-shaped second tray body having a deformable material therein moldable about at least some of a user's lower teeth, with subsequent setting and hardening of the molded material; and means for selectively coupling said upper and lower arch trays when the latter are installed on the user's upper and lower teeth respectively, said coupling means including adjustment structure for selective extension of the user's lower jaw, said first and second tray bodies each presenting an elongated adjustment slot of substantially L-shaped configuration therein oriented for permitting selective alteration of the arch configuration of the first and second bodies when said molding material therein is molded about a user's upper and lower teeth, with said bodies retaining said altered arch configuration after said setting and hardening of said molding material, in order to allow use thereof with a variety of users having different arch dimensions.

21. A dental device comprising:

an upper arch tray including a generally U-shaped first tray body having a deformable material therein moldable about at least some of a user's upper teeth, with subsequent setting and hardening of the molded material;

a lower arch tray including a generally U-shaped second tray body having a deformable material therein moldable about at least some of a user's lower teeth, with subsequent setting and hardening of the molded material, each of said first and second bodies further presenting an arcuate central bight having a pair of spaced, opposed ends and a leg member extending from each opposed end of said bight, said leg members diverging from each other; and means for selectively coupling said upper and lower arch trays when the latter are installed on the user's upper and lower teeth respectively, said coupling means including adjustment structure for selective extension of the user's lower jaw, said first and second tray bodies each presenting an elongated adjustment slot therein respectively located proximal to the corresponding bight ends and oriented for permitting selective alteration of the arch configuration of the first and second bodies when said molding material therein is molded about a user's upper and lower teeth, with said bodies retaining said altered arch configuration after said setting and hardening of said molding material, in order to allow use thereof with a variety of users having different arch dimensions.

22. A dental device comprising:

an upper arch tray including a generally U-shaped first tray body having a deformable material therein moldable about at least some of a user's upper teeth, with subsequent setting and hardening of the molded material;

a lower arch tray including a generally U-shaped second tray body having a deformable material therein moldable about at least some of a user's lower teeth, with subsequent setting and hardening of the molded material; and means for selectively coupling said upper and lower arch trays when the latter are installed on the user's upper and lower teeth respectively, said coupling means including adjustment structure for selective extension of the user's lower jaw, said first and second tray bodies each presenting an elongated adjustment slot therein oriented for permitting selective alteration of the arch configuration of the first and second bodies when said molding material therein is molded about a user's upper and lower teeth, with said bodies retaining said altered arch configuration after said setting and hardening of said molding material, in order to allow use thereof with a variety of users having different arch dimensions, each of said adjustment slots being generally L-shaped in configuration and extending from an outer margin of one of the sidewall segments of the corresponding body and through the entirety of the one sidewall segment, and through a substantial portion of the corresponding base panel.

* * * * *